United States Patent
Markwardt et al.

(10) Patent No.: US 11,173,267 B2
(45) Date of Patent: Nov. 16, 2021

(54) ADJUSTABLE TRACHEOSTOMA VALVE AND HEAT AND MOISTURE EXCHANGER

(71) Applicant: Freudenberg Medical, LLC, Carpinteria, CA (US)

(72) Inventors: Neil Markwardt, Santa Barbara, CA (US); John C. Day, Goleta, CA (US)

(73) Assignee: Freudenberg Medical, LLC, Carpinteria, CA (US)

( * ) Notice: Subject to any disclaimer, the term of this patent is extended or adjusted under 35 U.S.C. 154(b) by 449 days.

(21) Appl. No.: 16/223,670

(22) Filed: Dec. 18, 2018

(65) Prior Publication Data

US 2020/0188620 A1 Jun. 18, 2020

(51) Int. Cl.
| | | |
|---|---|---|
| *A61M 16/04* | (2006.01) | |
| *A61F 2/20* | (2006.01) | |
| *A61M 16/10* | (2006.01) | |
| *A61M 16/20* | (2006.01) | |

(52) U.S. Cl.
CPC ......... *A61M 16/0468* (2013.01); *A61F 2/203* (2013.01); *A61M 16/1045* (2013.01); *A61M 16/208* (2013.01)

(58) Field of Classification Search
CPC ............ A61M 16/0468; A61M 16/208; A61M 16/20; A62B 18/10; A63B 23/18
See application file for complete search history.

(56) References Cited

U.S. PATENT DOCUMENTS

| | | |
|---|---|---|
| 4,325,366 A | 4/1982 | Tabor |
| 4,582,058 A | 4/1986 | Depel et al. |
| 4,971,054 A | 11/1990 | Andersson et al. |
| 5,059,208 A | 10/1991 | Coe et al. |
| 5,738,095 A | 4/1998 | Persson |
| 5,806,515 A | 9/1998 | Bare et al. |

(Continued)

FOREIGN PATENT DOCUMENTS

| | | |
|---|---|---|
| EP | 3758912 A1 | 2/1997 |
| WO | 98/33543 A1 | 8/1998 |

(Continued)

OTHER PUBLICATIONS

Extended European Search Report dated May 7, 2020 (corresponding to EP 19 213 456.7).

*Primary Examiner* — Margaret M Luarca
(74) *Attorney, Agent, or Firm* — Harness, Dickey & Pierce, P.L.C.

(57) ABSTRACT

An adjustable tracheostoma valve includes a housing having a first opening that is adapted to open to a tracheostoma and a second opening that opens to ambient. The housing includes a lower housing portion defining the first opening and an upper housing portion movably attached to the lower housing portion and defining the second opening. A closure member is disposed in the housing and adapted to close the second opening. A flexible membrane includes a first region connected to the closure member and a plurality of spiral shaped legs extending from the first region and connected to the housing. The upper and lower housings are axially adjustable relative to one another to adjust an amount of air flow through the valve that would cause closure of the closure member. A heat and moisture exchanger is disposed in the housing between the first opening and the second opening.

23 Claims, 8 Drawing Sheets

(56) References Cited

U.S. PATENT DOCUMENTS

| | | |
|---|---|---|
| 6,193,751 B1 | 2/2001 | Singer |
| 6,422,235 B1 * | 7/2002 | Persson |
| 6,527,011 B1 * | 3/2003 | Mantz ................. A61M 16/208 |
| | | 128/203.11 |
| 6,772,758 B2 | 8/2004 | Lambert |
| 6,921,417 B2 | 7/2005 | Persson |
| 7,025,784 B1 | 4/2006 | Blom et al. |
| 7,059,327 B2 | 6/2006 | Worthington |
| 7,370,654 B2 | 5/2008 | Persson |
| 8,505,537 B2 | 8/2013 | Persson |
| 8,678,005 B2 | 3/2014 | Dawson |
| 8,887,718 B2 | 11/2014 | Shikani et al. |
| 8,944,063 B2 | 2/2015 | van der Houwen et al. |
| 8,991,394 B2 | 3/2015 | Persson |
| 2004/0193265 A1 | 9/2004 | Seder et al. |
| 2005/0178390 A1 | 8/2005 | Worthington |
| 2015/0083119 A1 | 3/2015 | Persson |
| 2015/0182715 A1 | 7/2015 | Bare et al. |
| 2015/0238718 A1 | 8/2015 | Schnell |
| 2016/0256649 A1 | 9/2016 | Hesselmar et al. |
| 2018/0207382 A1 | 7/2018 | Kamradt |

FOREIGN PATENT DOCUMENTS

| | | |
|---|---|---|
| WO | 99/29268 A1 | 6/1999 |
| WO | 2018/140351 A1 | 8/2018 |

\* cited by examiner

ADJUSTABLE TRACHEOSTOMA VALVE AND HEAT AND MOISTURE EXCHANGER

FIELD

The present disclosure relates to an adjustable tracheostoma valve and heat and moisture exchanger.

BACKGROUND

This section provides background information related to the present disclosure which is not necessarily prior art.

Loss of nasal function as a result of laryngectomy can result in functional changes to tracheal bronchial mucosa and lung function. These changes are due to dry cool air replacing the warm humid air which was provided by the function of the nose. A total laryngectomy surgery also results in a decreased resistance which has effect on lung function. These functional changes can result in an increase in mucus production, an increase in coughing, and an increase in chest infections.

Daily use of a heat and moisture exchanger (hereinafter HME) reduces loss of heat and moisture from the tracheal and bronchial mucosa and lungs, and provides the lungs with increased resistance. This warm, humidified and filtered air helps keep the mucosa from drying out and the increased resistance keeps the alveoli of the lungs from collapsing resulting in better lung function.

An adjustable tracheostoma valve (ATSV), is a vital component in tracheoesophageal voice restoration following total laryngectomy. Commonly referred to as a "Hands-free valve" it eliminates the need to cover the stoma with a thumb or finger to produce voice. The hands-free valve closes automatically when sufficient air pressure through the valve causes the valve to close and redirect the exhaled air through the voice prosthesis in order to allow the user to produce voice.

SUMMARY

This section provides a general summary of the disclosure, and is not a comprehensive disclosure of its full scope or all of its features.

An adjustable tracheostoma valve includes a housing having a first opening that is adapted to open to a tracheostoma and a second opening that opens to ambient. The housing includes a lower housing portion defining the first opening and an upper housing portion movably attached to the lower housing portion and defining the second opening. A closure member is disposed in the housing and adapted to close the second opening. A flexible membrane includes a first region connected to the closure member and a plurality of spiral shaped legs extending from the first region and connected to the housing. The upper and lower housings are axially adjustable relative to one another to adjust an amount of air flow through the valve that would cause closure of the closure member. A heat and moisture exchanger is disposed in the housing between the first opening and the second opening.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
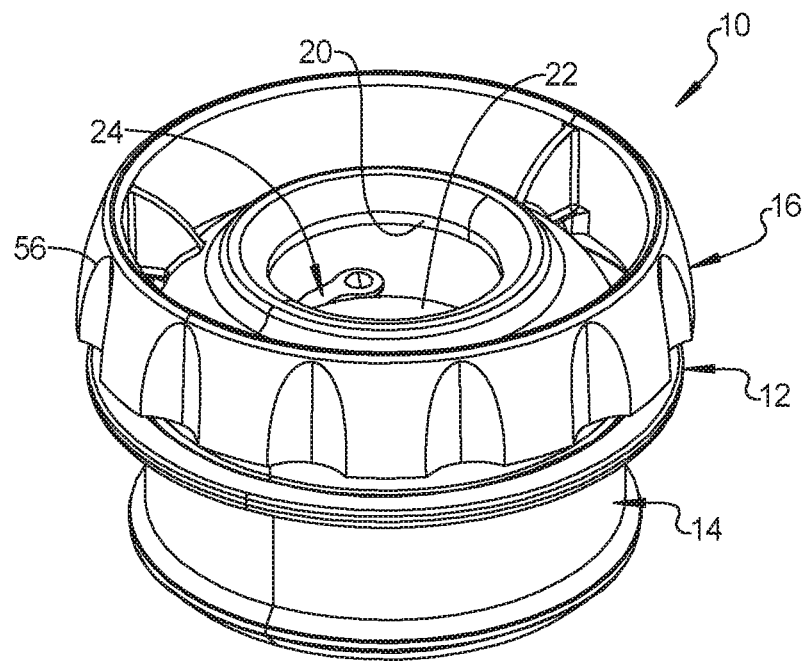
FIG. 1 is a top perspective view of an adjustable tracheostoma valve and heat and moisture exchanger according to the principles of the present disclosure.
Figure 2:
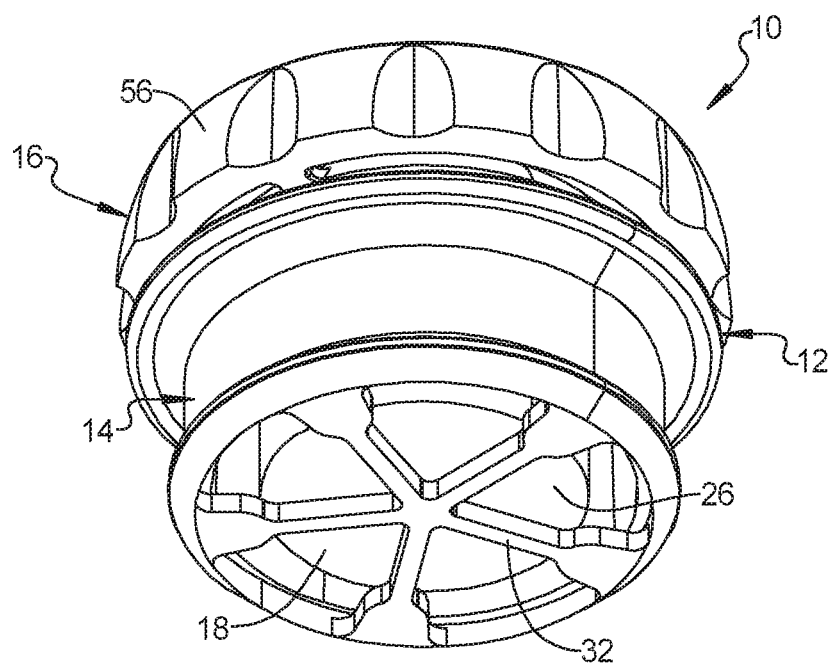
FIG. 2 is a bottom perspective view of the adjustable tracheostoma valve and heat and moisture exchanger shown in FIG. 1.
Figure 3:
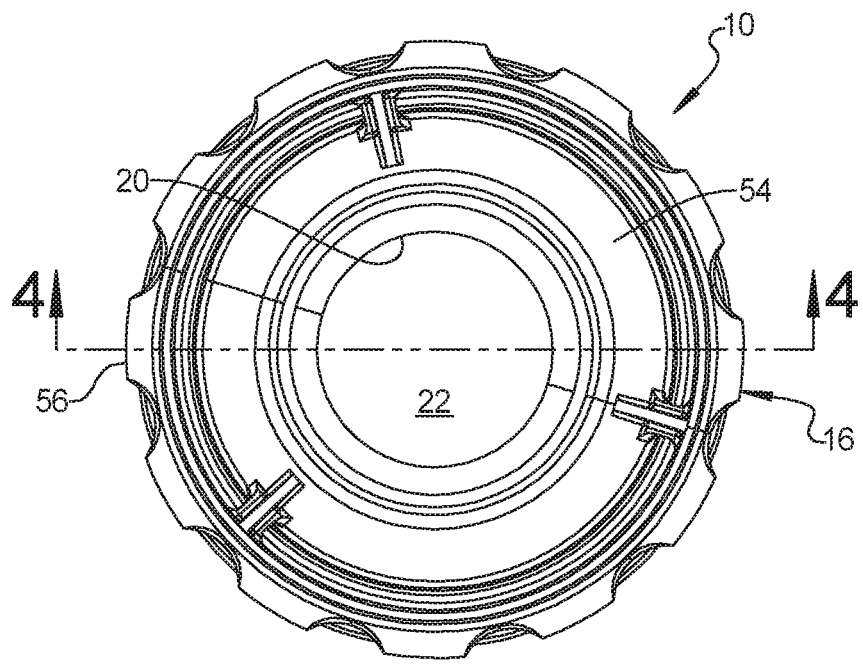
FIG. 3 is a top plan view of the adjustable tracheostoma valve and heat and moisture exchanger shown in FIG. 1.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to FIGS. 1-7, an adjustable tracheostoma valve 10 according to the principles the present disclosure will now be described. As shown in FIG. 1, the tracheostoma valve 10 includes a housing 12 including a lower housing portion 14 and an upper housing portion 16. The lower housing portion 14, best shown in FIG. 2, defines a first opening 18 that is adapted to open to a tracheostoma. The upper housing portion 16 defines a second opening 20 that opens to ambient, best shown in FIG. 1.

Figure 4:
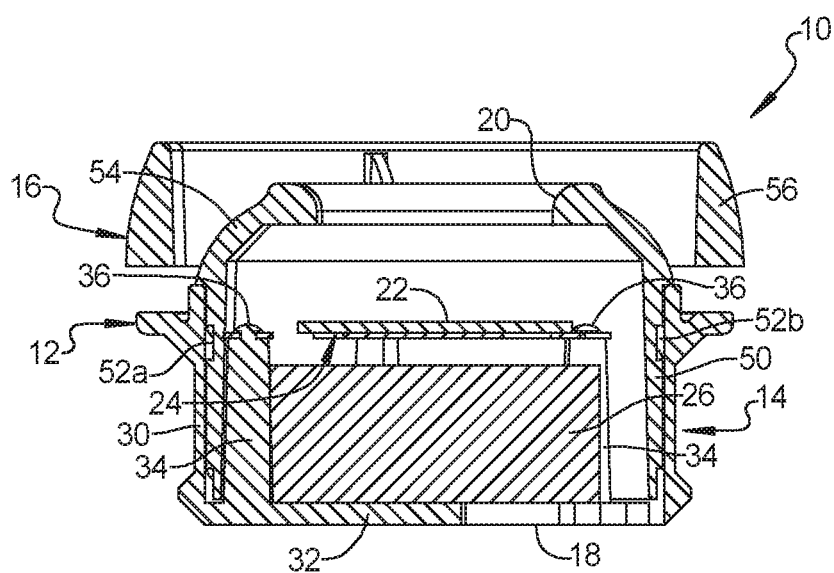
FIG. 4 is a cross-sectional view of the adjustable tracheostoma valve and heat and moisture exchanger shown in an open position.
Figure 5:
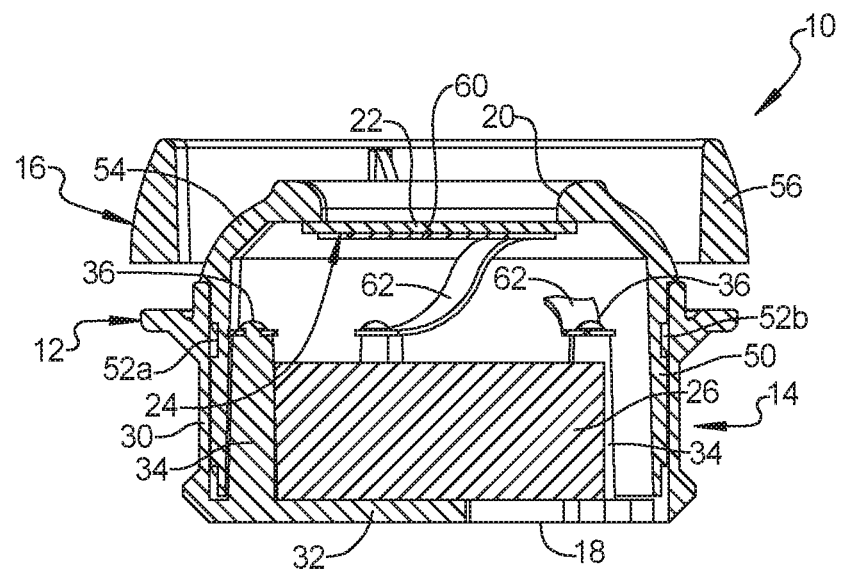
FIG. 5 is a cross-sectional view of the adjustable tracheostoma valve and heat and moisture exchanger shown in a closed position.
Figure 6:
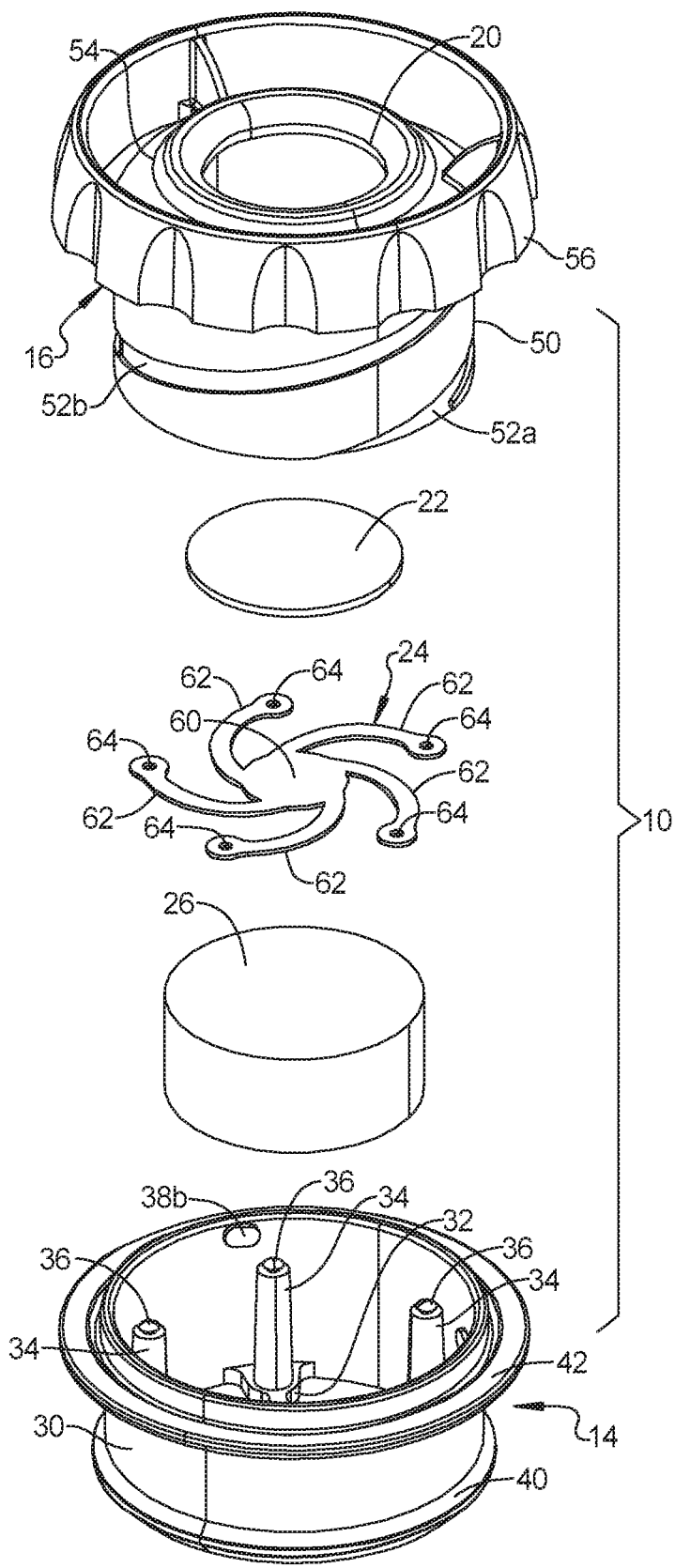
FIG. 6 is an exploded perspective view of the adjustable tracheostoma valve and heat and moisture exchanger shown in FIG. 1.

With reference to the cross-sectional views of FIGS. 4 and 5, the tracheostoma valve 10 includes a closure member 22 that is connected to a flexible membrane 24 (best shown in FIG. 6). The closure member 22 is movable between an open position as shown in FIG. 4 and a closed position as shown in FIG. 5. The flexible membrane 24 supports the closure member 22 generally in the position shown in FIG. 4 in a natural state and also when air is being inhaled through the tracheostoma valve 10. When air is being exhaled through the tracheostoma valve 10, the force of the air passing by the closure member 22 tends to cause the closure member 22 to move toward the second opening 20. When the force of air being exhaled is strong enough, the closure member 22 can be pressed fully against the second opening 20, as shown in FIG. 5 to redirect the exhaled air through the user's voice prosthesis to allow a user to produce voice. A humidifier filter 26 is disposed within the housing 12 between the first opening 18 and the closure member 22.

With reference to FIG. 6, an exploded perspective view of the adjustable tracheostoma valve 10 is shown. The lower housing 14 includes a cylindrical wall 30 and a grid 32 which extends across the first opening 18. The humidifier filter 26 is supported against the grid 32. A series of mounting posts 34 are disposed within the lower housing 14 and extend vertically from the grid 32 at a location spaced radially inward from the cylindrical wall 30. Each of the mounting posts 34 includes a respective peg 36 at a top end thereof. A plurality of protruding lugs 38a, 38b (only one of which is shown) extend from the inner surface of the cylindrical wall 30. A lower flange 40 can extend radially outward from a lower portion of the cylindrical wall 30 and can be adapted to snap into an adhesive base, as is known in the art. An upper flange 42 can extend radially outward from an upper portion of the cylindrical wall.

The upper housing 16 includes a cylindrical wall 50 having an outer surface with a pair of screw thread recesses 52a, 52b that are adapted to engage the pair of lugs 38a, 38b on the interior surface of the cylindrical wall 30 of the lower housing 14. The upper housing 16 includes a domed shape upper end 54 that defines the second opening 20. A handgrip flange 56 is connected to an upper portion of the cylindrical wall 50.

Figure 7:
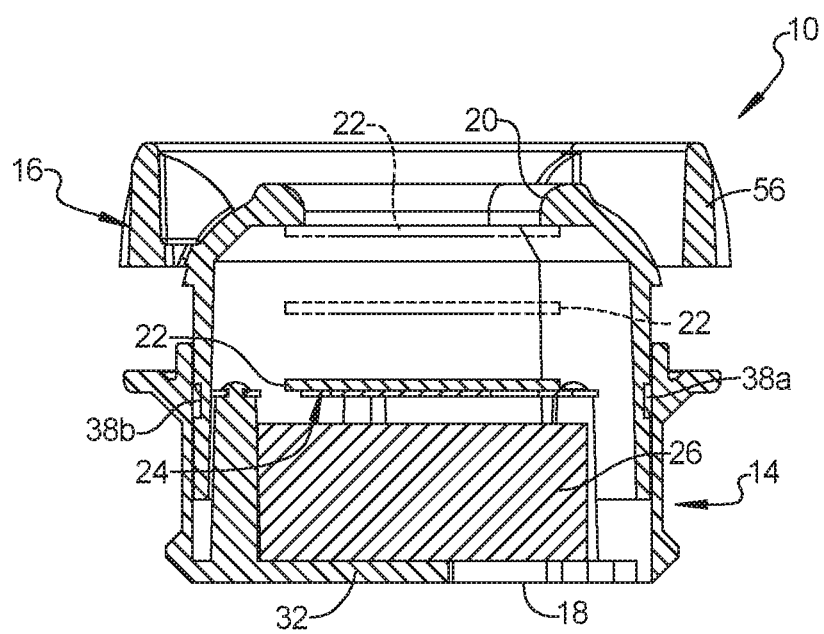
FIG. 7 is a cross-sectional view of the adjustable tracheostoma valve and heat and moisture exchanger shown in an adjusted position for increasing a closure force of the valve.

With reference to FIGS. 4 and 7, the engagement of the screw thread recesses 52a, 52b with the pair of lugs 38a, 38b allows the upper housing 16 to be rotated relative to the lower housing 14 to guide the upper housing to move axially relative to the lower housing 14 and cause the second opening 20 to move axially relative to the closure member 22. FIG. 4 shows the upper housing 16 fully received in the lower housing 14 to cause the closure member 22 to be at a closer distance from the second opening 20. FIG. 7 shows the axial position of the upper housing 16 to be extended relative to the lower housing 14 to cause the closure member 22 to be at a further distance from the second opening 20. Movement of the second opening 20 relative to the closure member 22 allows for adjustment of the air velocity that causes closure of the tracheostoma valve 10 in order to allow the tracheostoma valve to be easily adjusted for individual users.

The closure member 22 is in the form of a disk that can be formed from various materials. The closure member 22 is connected to a center region 60 of the flexible membrane 24, best shown in FIG. 6. The flexible membrane 24 includes a plurality of legs 62 extending from the center region 60. The plurality of legs 62 can be spiral-shaped and can include a distal end portion having an opening 64 adapted to receive the pegs 36 which can be heat staked or otherwise secured in order to securely mount the flexible membrane 24 to the posts 34 of the lower housing 14.

Figure 8:
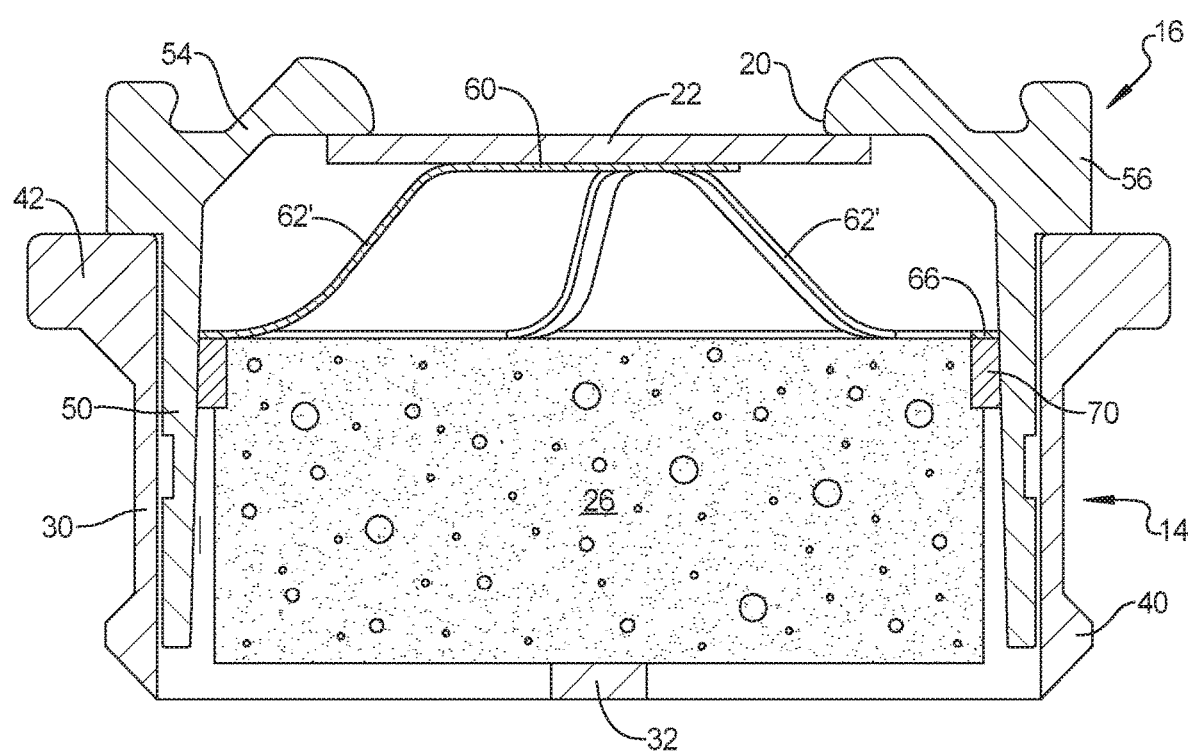
FIG. 8 is a cross-sectional view of an alternative adjustable tracheostoma valve and heat and moisture exchanger according to the principles of the present disclosure.
Figure 9:
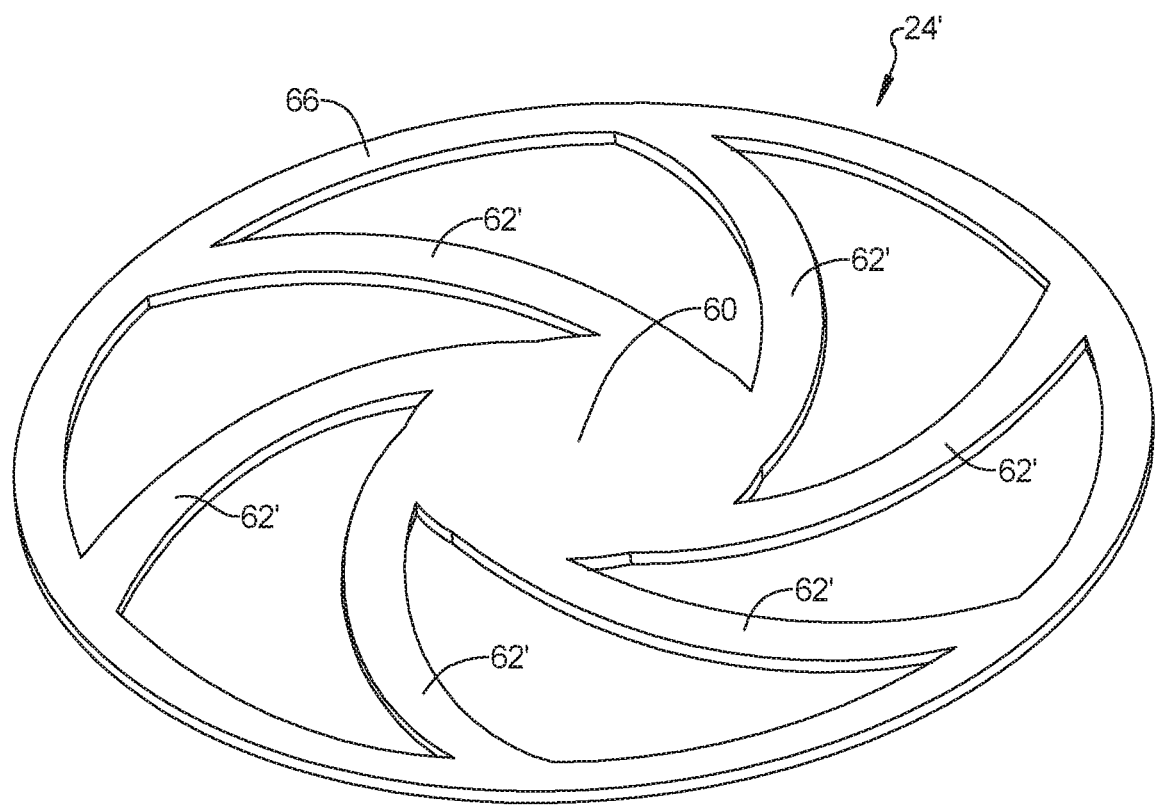
FIG. 9 is a perspective view of an alternative flexible membrane as shown in the alternative embodiment of FIG. 8.
Figure 10:
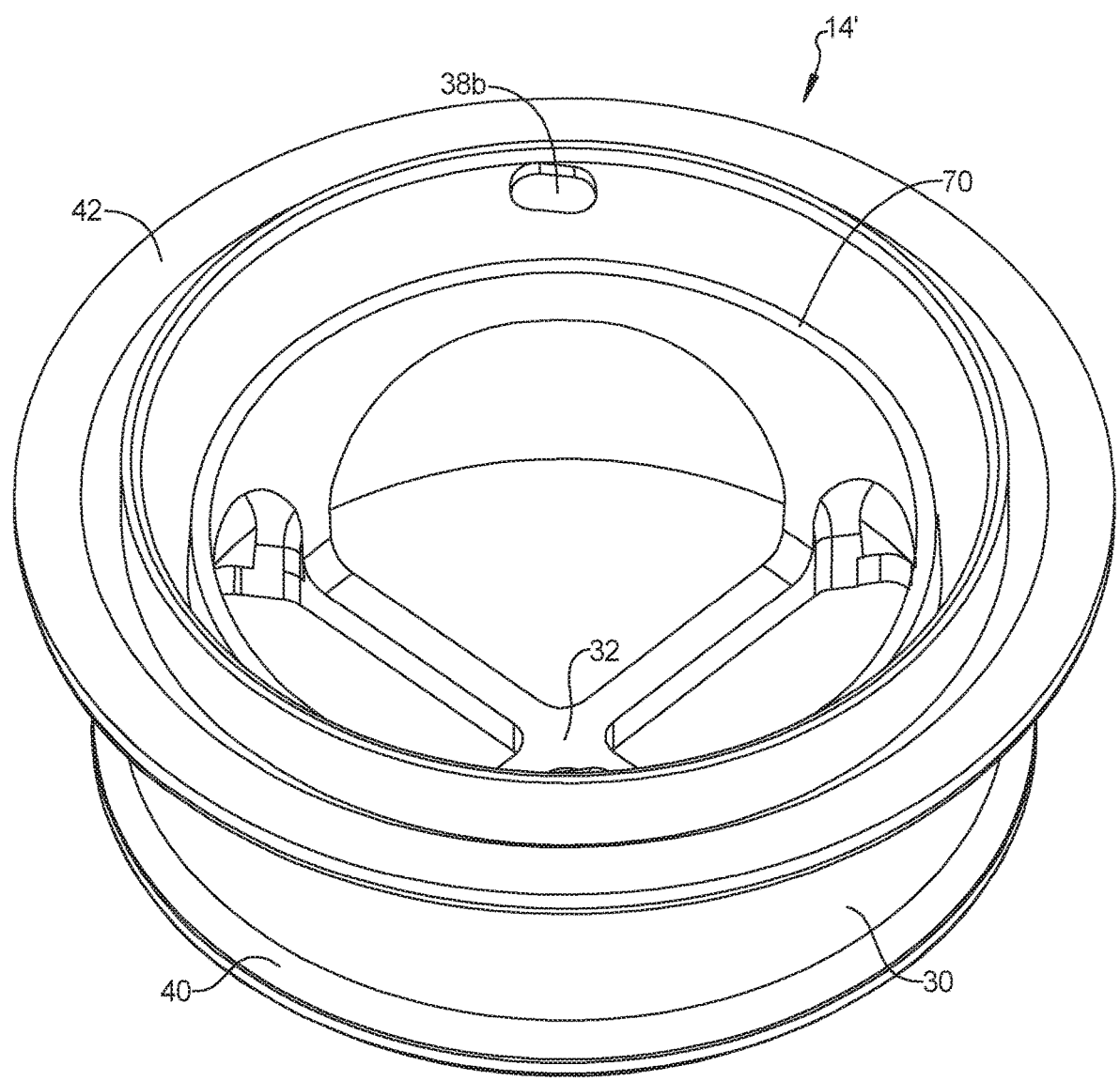
FIG. 10 is a perspective view of a lower housing of the adjustable tracheostoma valve shown in FIG. 8.

It should be noted that the flexible membrane 24 can take on various other forms and can be mounted to the lower housing 14 using different techniques. In an alternative embodiment, as shown in FIGS. 8-10, the flexible membrane 24' can include an outer circumferential ring 66 which is connected to the distal ends of each of the legs 62'. It should be understood that the flexible membranes 24, 24' can have two or more legs 62, 62'. Five legs 62 are shown in FIG. 6 and six legs 62' are shown in the embodiment of FIG. 9. With reference to FIGS. 8 and 10, the outer circumferential ring 66 can be mounted to posts and/or an upwardly extending ring structure 70 (best shown in FIG. 10) of the lower housing 14' using an adhesive, heat staking or other known attachment method.

Figure 11:
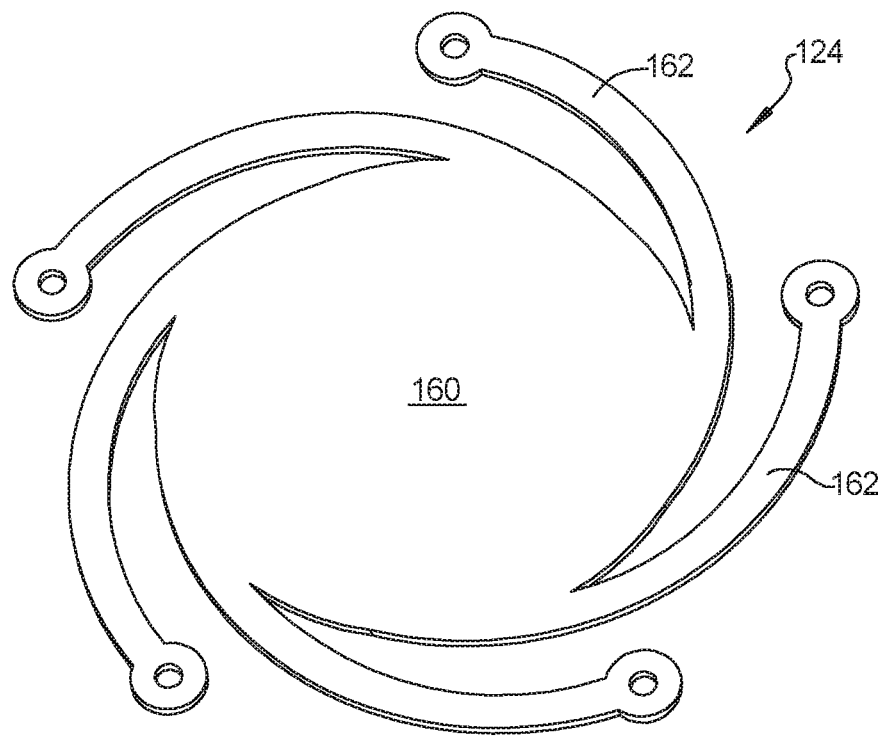
FIG. 11 is a perspective view of an alternative flexible membrane according to the principles of the present disclosure.
Figure 12:
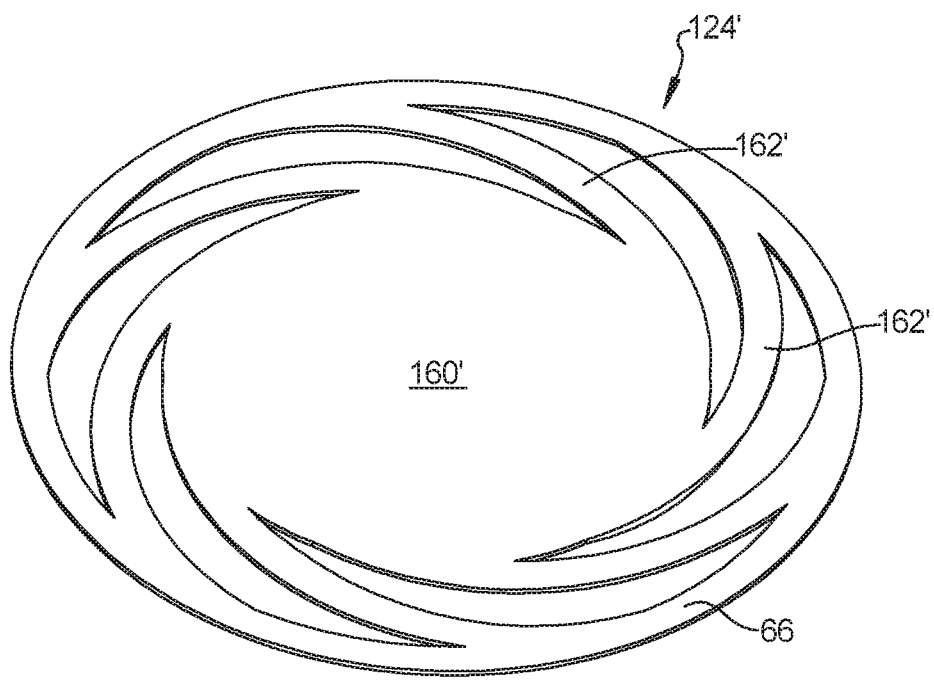
FIG. 12 is a perspective view of an alternative flexible membrane according to the principles of the present disclosure.

It is noted that the closure member 22 can be eliminated and, as shown in FIGS. 11 and 12 the center region 160/160' of the flexible membrane 124/124' can serve as an integrated closure member for covering the second opening 20. The diameter of the center region 160/160' can be chosen to be large enough to provide a proper closure for the second opening 20, while the legs 162/162' of the flexible membrane provide a connection to the lower housing in the same manner as described in the embodiments of FIGS. 1-7 and FIGS. 8-10. The center region 160/160' can be provided with an increased thickness and/or reinforcement ribs to assist the center region 160/160' with proper seating against the second opening 20.

In operation, the tracheostoma valve 10 is mounted with the first opening 18 disposed against a user's neck over top of a tracheostoma. As air is inhaled and exhaled through the tracheostoma valve 10, humidifier filter 26 reduces loss of heat and moisture to the environment. In addition, as sufficient air pressure is generated by exhalation through the tracheostoma valve 10, the closure member 22 can be caused to close off the second opening 20 to redirect the exhaled air through the voice prosthesis in order to allow the user to produce voice. Because different patients breathe at different air velocities, the tracheostoma valve 10 can be adjusted to the patient's comfort level by adjusting the position of the upper housing 16 relative to the lower housing 14 and reducing or extending the distance between the closure member 22 and the second opening 20.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tracheostoma valve, comprising:
   a housing having a first opening that is adapted to open to a tracheostoma and a second opening that opens to ambient;
   a closure member disposed in the housing and adapted to close one of the first opening and the second opening; and
   a flexible membrane including a first region connected to the closure member and a plurality of legs formed integral with and extending from the first region and connected to the housing, wherein in an un-deformed state, the plurality of legs are coplanar with the first region and extend radially outward from the first region in a spiral shape and terminate at a free-end in an unassembled state.

2. The tracheostoma valve according to claim 1, wherein the plurality of legs are connected to the housing by a plurality of respective pegs that are affixed within an opening in an end of the plurality of legs.

3. The tracheostoma valve according to claim 2, wherein the plurality of respective pegs are disposed on a respective one of a plurality of posts within the housing.

4. The tracheostoma valve according to claim 1, further comprising a heat and moisture exchanger disposed in the housing between the first opening and the second opening.

5. The tracheostoma valve according to claim 1, wherein the housing includes a lower housing portion defining the first opening and an upper housing portion movably attached to the lower housing portion and defining the second opening.

6. The tracheostoma valve according to claim 5, wherein the flexible membrane is connected to the lower housing portion of the housing.

7. The tracheostoma valve according to claim 5, wherein the upper housing portion is axially movable relative to the lower housing portion.

8. A tracheostoma valve, comprising:
   a housing having a first opening that is adapted to open to a tracheostoma and a second opening that opens to ambient;
   a closure member disposed in the housing and adapted to close the second opening; and
   a flexible membrane including a first region connected to the closure member and a plurality of spiral shaped legs extending from the first region and connected to the housing, wherein in an un-deformed state, the plurality of spiral shaped legs are coplanar with the first region and terminate at a free-end in an unassembled state.

9. The tracheostoma valve according to claim 8, wherein the plurality of spiral shaped legs are connected to the housing by a plurality of respective pegs that are affixed within an opening in an end of the plurality of spiral shaped legs.

10. The tracheostoma valve according to claim 9, wherein the plurality of respective pegs are disposed on a respective one of a plurality of posts within the housing.

11. The tracheostoma valve according to claim 8, further comprising a heat and moisture exchanger disposed in the housing between the first opening and the second opening.

12. The tracheostoma valve according to claim 8, wherein the housing includes a lower housing portion defining the first opening and an upper housing portion movably attached to the lower housing portion and defining the second opening.

13. The tracheostoma valve according to claim 12, wherein the flexible membrane is connected to the lower housing portion of the housing.

14. The tracheostoma valve according to claim 12, wherein the upper housing portion is axially movable relative to the lower housing portion.

15. An adjustable tracheostoma valve, comprising:
    a housing having a first opening that is adapted to open to a tracheostoma and a second opening that opens to ambient, wherein the housing includes a lower housing portion defining the first opening and an upper housing portion movably attached to the lower housing portion and defining the second opening;
    a closure member disposed in the housing and adapted to close the second opening;
    a flexible membrane including a first region connected to the closure member and a plurality of spiral shaped legs extending from the first region and connected to the housing, wherein in an un-deformed state, the plurality of spiral shaped legs are coplanar with the first region and terminate at a free-end in an unassembled state; and
    a heat and moisture exchanger disposed in the housing between the first opening and the second opening.

16. A tracheostoma valve, comprising:
    a housing having a first opening that is adapted to open to a tracheostoma and a second opening that opens to ambient; and
    a flexible membrane including a center region adapted to close one of the first opening and the second opening and a plurality of legs extending from the center region and connected to the housing, wherein in an un-deformed state, the plurality of legs are coplanar with the first region and extend radially outward from the first region in a spiral shape and terminate at a free-end in an unassembled state.

17. The tracheostoma valve according to claim 16, wherein the plurality of legs are connected to the housing by a plurality of respective pegs that are affixed within an opening in an end of the plurality of legs.

18. The tracheostoma valve according to claim 17, wherein the plurality of respective pegs are disposed on a respective one of a plurality of posts within the housing.

19. The tracheostoma valve according to claim 16, further comprising a heat and moisture exchanger disposed in the housing between the first opening and the second opening.

20. The tracheostoma valve according to claim 16, wherein the housing includes a lower housing portion defining the first opening and an upper housing portion movably attached to the lower housing portion and defining the second opening.

21. The tracheostoma valve according to claim 20, wherein the flexible membrane is connected to the lower housing portion of the housing.

22. The tracheostoma valve according to claim 20, wherein the upper housing portion is axially movable relative to the lower housing portion.

23. An adjustable tracheostoma valve, comprising:

a housing having a first opening that is adapted to open to a tracheostoma and a second opening that opens to ambient, wherein the housing includes a lower housing portion defining the first opening and an upper housing portion movably attached to the lower housing portion and defining the second opening;

a flexible membrane including a center region adapted to close one of the first opening and the second opening and a plurality of spiral shaped legs extending from the center region and connected to the housing, wherein in an un-deformed state, the plurality of spiral shaped legs are coplanar with the first region and terminate at a free-end in an unassembled state; and a heat and moisture exchanger disposed in the housing between the first opening and the second opening.

\* \* \* \* \*